United States Patent
Kanniah et al.

(10) Patent No.: US 9,212,172 B2
(45) Date of Patent: Dec. 15, 2015

(54) PREPARATION OF CRYSTALLINE BAZEDOXIFENE AND ITS SALTS

(75) Inventors: Sundra Lakshmi Kanniah, Vellore District (IN); Rajesham Boge, Hyderabad (IN); Peddireddy Subbareddy, YSR District (IN); Lalita Kanwar, Bangalore (IN); Srividya Ramakrishnan, Hyderabad (IN); Ramya Kumar, Hyderabad (IN); Rakeshwar Bandichhor, Sultanpur (IN); Amarnath Reddy Lekkala, Hyderabad (IN); Ravi Kumar Mylavarapu, Medak District (IN); Vagwala Raghunath, Hyderabad (IN)

(73) Assignees: DR. REDDY'S LABORATORIES LIMITED, Hyderabad (IN); DR. REDDY'S LABORATORIES, INC., Bridgewater, NJ (US)

( * ) Notice: Subject to any disclaimer, the term of this patent is extended or adjusted under 35 U.S.C. 154(b) by 81 days.

(21) Appl. No.: 13/822,519

(22) PCT Filed: Sep. 14, 2011

(86) PCT No.: PCT/US2011/051501
§ 371 (c)(1),
(2), (4) Date: May 9, 2013

(87) PCT Pub. No.: WO2012/037187
PCT Pub. Date: Mar. 22, 2012

(65) Prior Publication Data
US 2013/0225805 A1  Aug. 29, 2013

Related U.S. Application Data
(60) Provisional application No. 61/409,197, filed on Nov. 2, 2010, provisional application No. 61/473,980, filed on Apr. 11, 2011.

(30) Foreign Application Priority Data
Sep. 14, 2010  (IN) ............................ 2686/CHE/2010
Feb. 25, 2011  (IN) ............................. 563/CHE/2011

(51) Int. Cl.
C07D 403/10   (2006.01)
C07D 403/12   (2006.01)
C07D 209/12   (2006.01)

(52) U.S. Cl.
CPC ............ C07D 403/12 (2013.01); C07D 209/12 (2013.01)

(58) Field of Classification Search
CPC ............................ C07D 403/10; C07D 403/12
USPC ........................................................ 540/602
See application file for complete search history.

(56) References Cited

U.S. PATENT DOCUMENTS

| | | | |
|---|---|---|---|
| 5,998,402 A | 12/1999 | Miller et al. | |
| 6,005,102 A | 12/1999 | Raveendranath et al. | |
| 6,479,535 B1 | 11/2002 | Pickar et al. | |
| 7,683,051 B2 | 3/2010 | Demerson et al. | |
| 7,683,052 B2 | 3/2010 | Ali et al. | |
| 8,063,041 B2 * | 11/2011 | Andreella et al. | 514/217.08 |
| 8,183,367 B2 | 5/2012 | Andreella et al. | |
| 2005/0227964 A1 | 10/2005 | Fawzi et al. | |
| 2010/0016290 A1 | 1/2010 | Cotarca et al. | |
| 2010/0016582 A1 | 1/2010 | Soriato et al. | |
| 2010/0240888 A1 | 9/2010 | Jirman et al. | |

FOREIGN PATENT DOCUMENTS

EP   0802183 A1   10/1997

OTHER PUBLICATIONS

International Search Report dated, Apr. 19, 2012 for corresponding International Patent Application No. PCT/US2011/051501.

* cited by examiner

*Primary Examiner* — Brenda Coleman
(74) *Attorney, Agent, or Firm* — Pergament Gilman & Cepeda LLP; Milagros A. Cepeda; Edward D. Pergament

(57) ABSTRACT

Aspects of the present disclosure include crystalline bazedoxifene free base, crystalline bazedoxifene acetate Form D, and processes for their preparation. The drug compound having the adopted name "bazedoxifene acetate" has a chemical name 1-[4-(2-azepan-1-yl-ethoxy)benzyl]-2-(4-hydroxyphenyl)-3-methyl-1H-indol-5-ol acetic acid, and has the chemical structure shown below as Formula I.

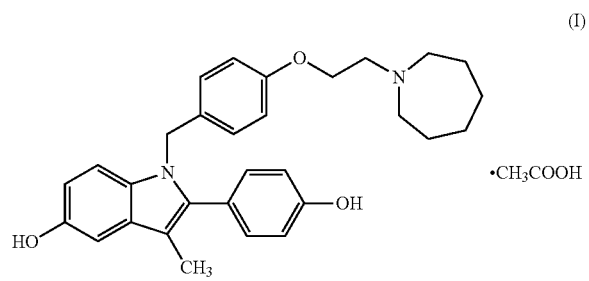

24 Claims, 8 Drawing Sheets

PREPARATION OF CRYSTALLINE BAZEDOXIFENE AND ITS SALTS

This application is a National Stage Application under 35 U.S.C. 371 of PCT International Application No. PCT/US2011/051501, filed Sep. 14, 2011, which claims priority to Indian Provisional Applications 2686/CHE/2010, filed on Sep. 14, 2010, 563/CHE/2011, filed on Feb. 25, 2011 and U.S. Provisional Applications Nos. 61/409,197, filed on Nov. 2, 2010, 61/473,980, filed on Apr. 11, 2011; all of which are hereby incorporated by reference in their entirety.

INTRODUCTION

Aspects of the present disclosure include crystalline bazedoxifene free base, crystalline bazedoxifene acetate Form D, and processes for their preparation.

The drug compound having the adopted name "bazedoxifene acetate" has a chemical name 1-[4-(2-azepan-1-yl-ethoxy)benzyl]-2-(4-hydroxyphenyl)-3-methyl-1H-indol-5-ol acetic acid, and has the chemical structure shown below as Formula I.

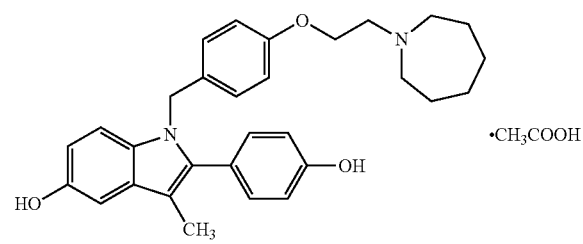

Bazedoxifene acetate belongs to the class of drugs typically referred to as selective estrogen receptor modulators (SERMs). Consistent with its classification, bazedoxifene demonstrates affinity for estrogen receptors (ER), but shows tissue selective estrogenic effects. For example, bazedoxifene is estrogenic on bone and cardiovascular lipid parameters and antiestrogenic on uterine and mammary tissue and thus has the potential for treatment and prevention of bone tissue loss, replacement of estrogen and prevention of heart and vein diseases in post-menopausal women.

The preparation of bazedoxifene and its salts is described in U.S. Pat. Nos. 5,998,402, 6,479,535, and 6,005,102. An article by C. P. Miller et al., "Design, Synthesis, and Preclinical Characterization of Novel, Highly Selective Indole Estrogens," *Journal of Medicinal Chemistry*, Vol. 44, pages 1654-1657, 2001, also reports the synthetic preparation of bazedoxifene acetate. In these documents, bazedoxifene free base is obtained by debenzylation of dibenzylated bazedoxifene, which was subjected to purification by column chromatography to achieve sufficient purity and then isolated in the form of white or tan foam by evaporation of solvent. However, the existence or preparation of crystalline bazedoxifene free base is not disclosed in the documents.

European Patent Application No. 0802183 describes a synthesis of bazedoxifene 5-Benzyloxy-2(4-benzyloxyphenyl)-1-[4-(2-bromoethoxy)benzyl]-3-methyl-indole is reacted with azepan, under suitable reaction conditions, followed by deprotection to yield bazedoxifene, which on subsequent treatment with acetone and acetic acid gives bazedoxifene acetate.

Three crystalline polymorphic forms of bazedoxifene acetate are disclosed in U.S. Pat. Nos. 7,683,051 and 7,683,052, and in International Application Publication No. WO 2009/012734 A3. An amorphous form is described in International Application Publication No. WO 2009/102778 A1, International Application Publication No. WO 2009/102771 A1, and International Application Publication No. WO 2009/102773 A1 relate to processes for preparation of polymorphic Form A of bazedoxifene acetate. International Application Publication Nos. WO 2009/012734 A2 pertain to salts of bazedoxifene with polycarboxylic acids, methods of preparation, a method of purification of bazedoxifene by preparation of a salt of bazedoxifene with a polycarboxylic acid, and a polymorphic form of bazedoxifene acetate designated as Form C.

In the development of pharmaceutical compositions, crystallinity is a desirable property for an active pharmaceutical ingredient. Crystal substances facilitate processing and formulating into most types of pharmaceutical dosage forms. Further, it would be advantageous to employ a crystalline free base as a starting material for preparation of bazedoxifene acetate, to achieve high purity.

Polymorphism, the occurrence of different crystal forms, is a property of some molecules and molecular complexes. A single molecule, like bazedoxifene acetate, may give rise to a variety of crystalline forms having distinct crystal structures and physical properties like melting point, x-ray diffraction pattern, infrared absorption fingerprint, and solid state NMR spectrum. One crystalline form may give rise to thermal behavior different from that of another crystalline form. Thermal behavior can be measured in the laboratory by such techniques as capillary melting point, thermogravimetric analysis ("TGA"), or differential scanning calorimetry ("DSC"), which have been used to distinguish polymorphic forms.

The difference in the physical properties of different crystalline forms results from the orientation and intermolecular interactions of adjacent molecules or complexes in the bulk solid. Accordingly, polymorphs are distinct solids sharing the same molecular formula yet having advantageous physical properties compared to other crystalline forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different crystalline forms or polymorphs of the same pharmaceutical compounds can and reportedly do have different aqueous solubilities.

The discovery of new polymorphic forms or solvates of a pharmaceutically useful compound provides a new opportunity to improve the performance characteristics of a pharmaceutical product. It enlarges the repertoire of materials that a formulation scientists has available for designing, for example, a pharmaceutical dosage form of a drug with a targeted release profile or other desired characteristics. Therefore, there is a need for additional crystalline forms of bazedoxifene acetate.

Since improved drug formulations are consistently sought, there is an ongoing need for new or purer polymorphic form of existing drug molecules. The present invention describes polymorph of bazedoxifene free base and acetate salt that helps to meet aforementioned and other needs.

SUMMARY

Aspects of the present disclosure provide processes for the preparation of crystalline bazedoxifene free base and acetate salt.

An aspect of the present disclosure provides processes for preparing crystalline form of bazedoxifene free base, embodiments comprising:
 a) either reacting an acid addition salt of bazedoxifene with a base to form bazedoxifene free base; or
 b) adjusting the pH of the aqueous phase of a mixture of an acid addition salt of bazedoxifene and a solvent comprising water to about 7-10 using a suitable base; and
 c) isolating the crystalline bazedoxifene free base.

The isolated crystalline bazedoxifene free base can be present in any form which include but not limited to the anhydrate, a solvate, or a hydrate.

An aspect of the present disclosure includes anhydrous crystalline bazedoxifene free base, designated as "Form A" that can be characterized by using any of various analytical techniques, such as powder X-ray diffraction (PXRD), differential scanning calorimetry (DSC), thermogravimetric analysis (TGA), or Fourier-transform infrared (FT-IR) spectroscopy.

An aspect of the present disclosure includes crystalline anhydrous bazedoxifene acetate designated herein as "Form D," that can be characterized by any of analytical techniques such as PXRD, DSC, TGA, or FT-IR.

An aspect of the present disclosure provides processes for preparing crystalline bazedoxifene acetate designated as Form D, embodiments comprising at least one of the steps:
 a) providing bazedoxifene free base in a suitable solvent;
 b) adding a source of acetate ion to the mixture of step a); and
 c) maintaining the mixture of step b) for a time and under conditions suitable for formation of crystalline bazedoxifene acetate.

Another aspect of the present disclosure provides processes for preparing a crystalline form of bazedoxifene acetate designated as Form D, embodiments comprising at least one of the steps:
 a) providing a mixture of bazedoxifene acetate in a suitable solvent;
 b) adding seed crystals of crystalline bazedoxifene acetate Form D and an anti-solvent; and
 c) isolating crystalline Form D of bazedoxifene acetate.

DETAILED DESCRIPTION

Figure 1:
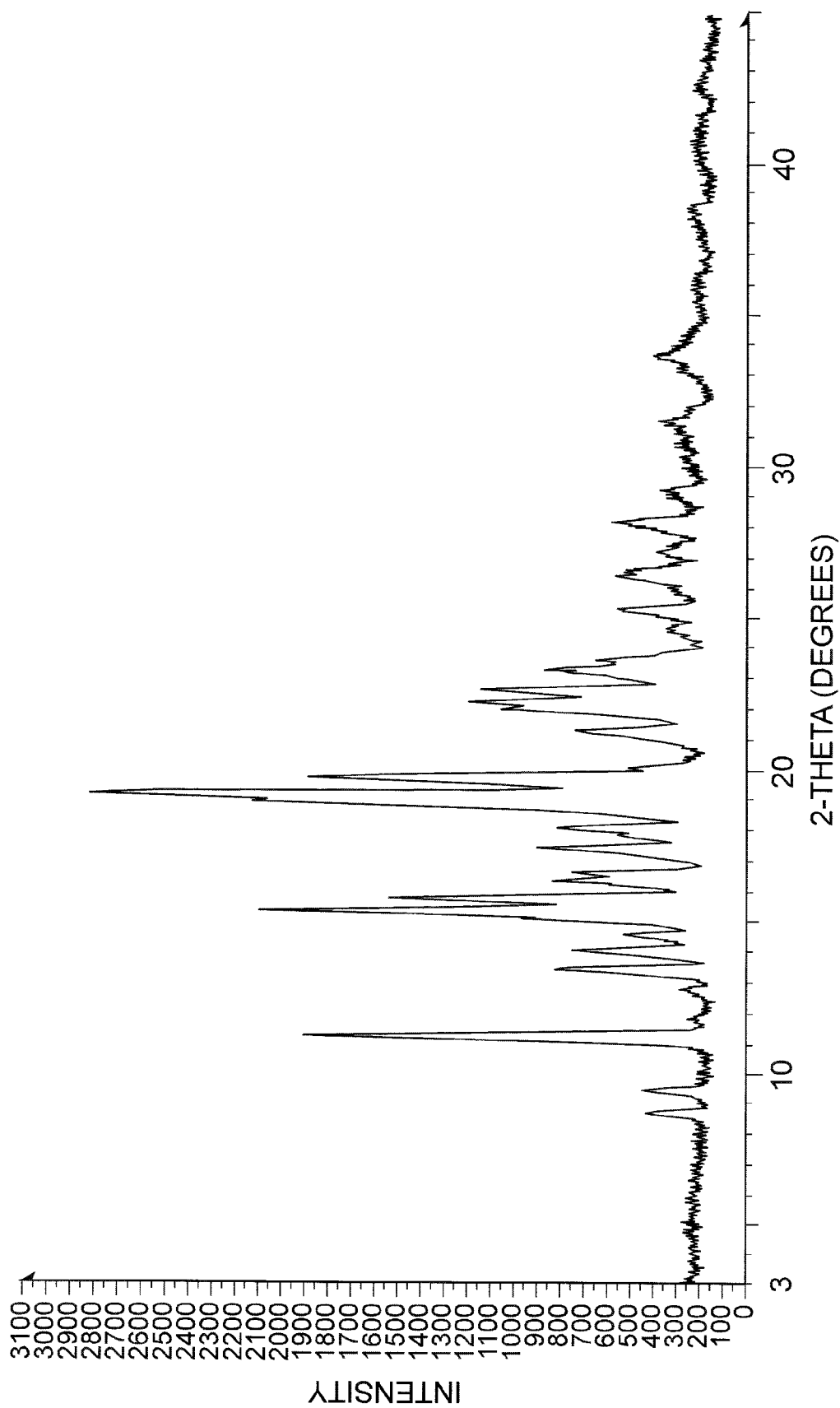
FIG. 1 is a PXRD pattern of crystalline bazedoxifene free base obtained in accordance with Example 3
Figure 2:
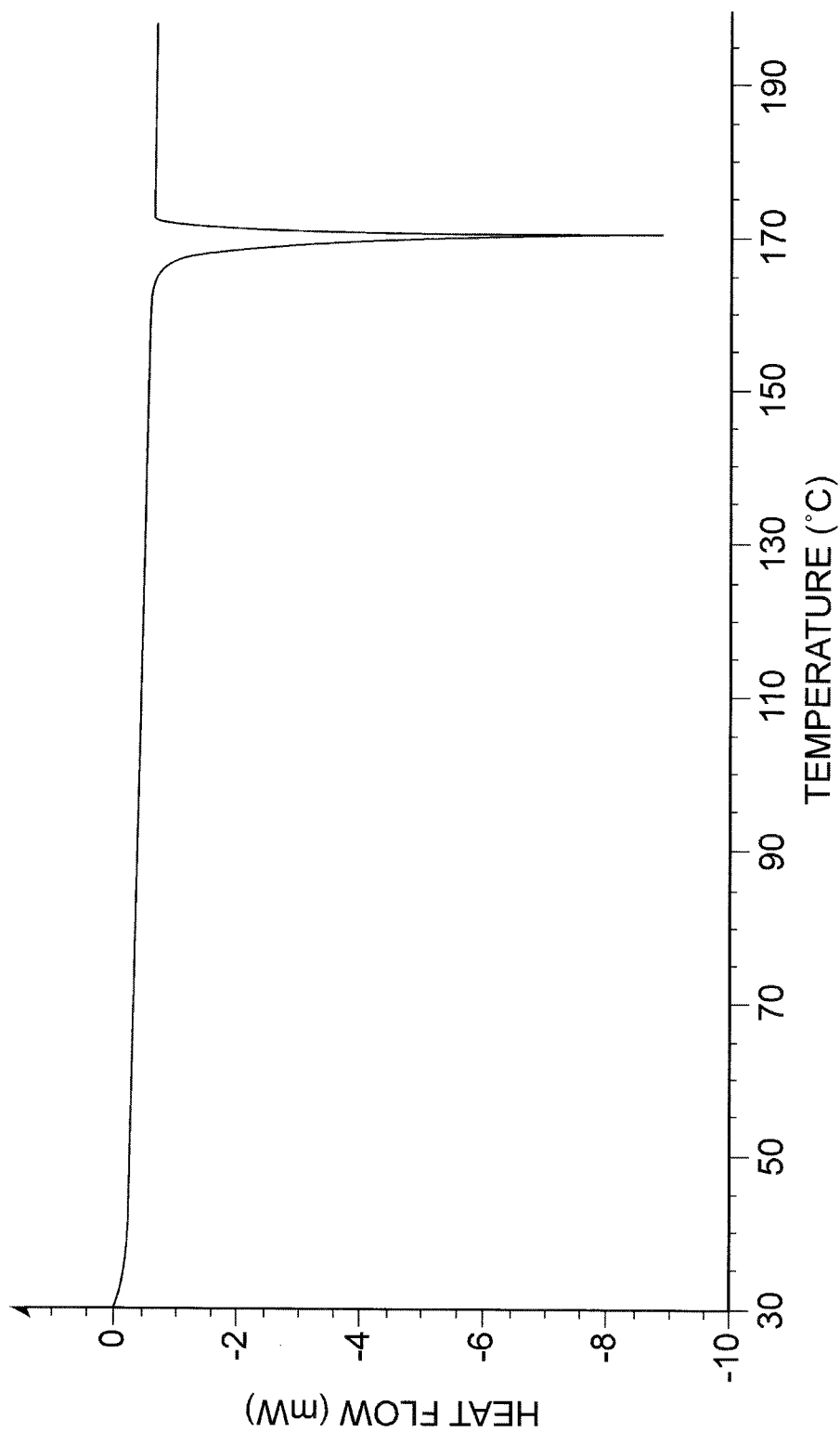
FIG. 2 is a DSC curve of crystalline bazedoxifene free base obtained in accordance with Example 3
Figure 3:
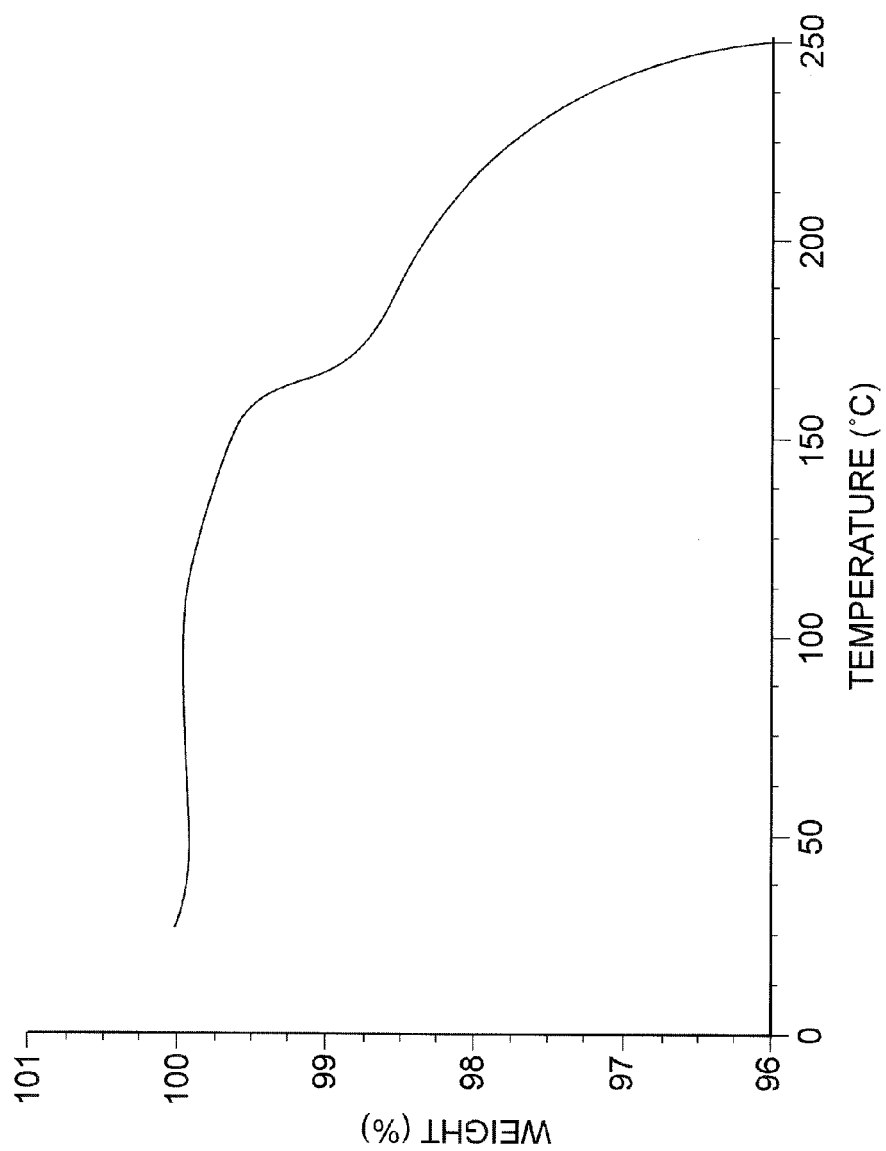
FIG. 3 is a TGA curve of crystalline bazedoxifene free base obtained in accordance with Example 3

An aspect of the present disclosure provides processes for preparing crystalline bazedoxifene free base, embodiments comprising:
 a) either reacting an acid addition salt of bazedoxifene with a base to form bazedoxifene free base; or
 b) adjusting the pH of the aqueous phase of a mixture of an acid addition salt of bazedoxifene and a solvent comprising water to about 7-10 using a suitable base; and
 c) isolating the crystalline bazedoxifene free base.

The mixture comprising bazedoxifene acid addition salt in step a) may be a suspension or a solution. A mixture comprising a bazedoxifene acid addition salt may be obtained by providing isolated bazedoxifene acid addition salt in a suitable solvent or such a mixture may be obtained directly from a reaction in which a bazedoxifene acid addition salt is formed.

If it is intended to obtain a clear solution of bazedoxifene free base or its salt, the reaction mixture can be heated to dissolution temperature that can be any temperature as long as the stability of the bazedoxifene or its salt is not compromised and a substantially clear solution is obtained. For example, the dissolution temperature may range from about 20° C. to about the reflux temperature of the solvent.

Solvents employed for preparation of a crystalline form of bazedoxifene free base include, but are not limited to: alcohols, such as, for example, methanol, ethanol, or 2-propanol; ethers, such as, for example, diisopropyl ether, methyl tert-butyl ether, diethyl ether, 1,4-dioxane, THF, or methyl THF; esters, such as, for example, ethyl acetate, isopropyl acetate, or t-butyl acetate; ketones such as acetone or methyl isobutyl ketone; halogenated hydrocarbons, such as, for example, dichloromethane, dichloroethane, chloroform, or the like; hydrocarbons, such as, for example, toluene, xylene, or cyclohexane; nitriles such as acetonitrile; dipolar aprotic solvents such as dimethyl formamide, dimethyl acetamide, dimethyl sulfoxide or like; water; or any mixtures thereof.

Alternately, bazedoxifene free base can be generated by following the process of step b). In step b), for generation of bazedoxifene free base from its salt, a base can be added in one lot to the mixture comprising bazedoxifene acid addition salt, or the pH of the aqueous phase can be adjusted to a range from about 7 to about 10, or about 8 to about 9, by addition of base as a solution or in neat form. Bases employed for such purpose in step b) include, but are not limited to: inorganic bases such as alkali metal hydroxides or carbonates; or organic bases such as pyridine, lutidine, triethylamine, 4-dimethylaminopyridine (DMAP), dicyclohexylamine, diisopropylethylamine, morpholine, N-methylmorpholine, or ammonium hydroxide; or the like. Suitable times for crystallization will vary, and can be from about 10 minutes to about 10 hours, or longer. Suitable temperatures for crystallization are about −10 to about 50° C., about 10 to about 30° C., or any other temperatures may be used. Amounts of solvent per gram of bazedoxifene acid addition salt will vary and, in embodiments, can be from 5 mL to about 100 mL. Once obtained, crystals of bazedoxifene Form A may be used as the nucleating agent or "seed" crystals for subsequent crystallizations of Form A of bazedoxifene free base from the crystallization solvent.

Step c) involves isolation of the solid obtained in step b) by any methods to afford the desired crystalline form of bazedoxifene free base.

The methods by which the solid material is isolated from the reaction mixture, with or without cooling below the operating temperature, induced by seeding, may be any of techniques such as filtration by gravity, filtration by suction, centrifugation, evaporation, or the like, or combinations thereof. The crystals so isolated can carry a small proportion of occluded mother liquor containing a higher percentage of impurities. If desired the crystals may be washed with a suitable solvent.

The isolated crystalline bazedoxifene free base can be present in any form which include but not limited to the anhydrate, solvate, or hydrate.

Crystalline bazedoxifene free base may be used as a synthetic intermediate to prepare a bazedoxifene pharmaceutically acceptable acid addition salt, such as bazedoxifene acetate or bazedoxifene ascorbate. The crystalline bazedoxifene free base may be dissolved in a solvent and reacted with an acid, to form a pharmaceutically acceptable acid addition salt. The crystallization of bazedoxifene free base can further improve the purity of acid addition salt of bazedoxifene. In one embodiment crystalline bazedoxifene free base is an anhydrate crystalline form designated as Form A.

An aspect of the present disclosure includes anhydrous crystalline bazedoxifene free base, designated as "Form A" that can be characterized by using any of various analytical techniques, such as powder X-ray diffraction (PXRD), differential scanning calorimetry (DSC), thermogravimetric analysis (TGA), or Fourier-transform infrared (FT-IR) spectroscopy. For example, there is provided a novel crystalline Form A of bazedoxifene free base characterized by its powder X-ray diffractogram with peaks at 11.28, 15.41, 15.82, 19.02, 19.26, 19.82, 22.30, 22.70 degrees of 2θ values, a PXRD pattern with peaks further at about 13.47, 14.12, 14.61, 16.47, 16.66, 17.50, 18.17, 23.35, 23.72 degrees of 2θ values, a PXRD pattern with peaks further at about 8.71, 9.47, 11.85, 12.80, 20.19, 21.34, 22.16, 24.71, 25.36, 26.48, 28.22, 29.28, 33.70 degrees of 2θ values.

Yet another aspect of the present disclosure includes crystalline anhydrous Form D of bazedoxifene acetate. Form D can be characterized by any of PXRD, DSC, TGA, or FT-IR. For example, there is provided a novel crystalline anhydrous Form D of bazedoxifene acetate characterized by its powder X-ray diffractogram with peaks at 5.87, 7.83, 11.73, 17.73 degrees of 2θ values, a PXRD pattern with peaks further at about 12.84, 13.40, 19.91, 23.30, 34.63 degrees of 2θ values, a PXRD pattern with peaks further at about 9.91, 15.69, 17.11, 20.51 degrees of 2θ values. The skilled artisan will realize that the precise value of melting point will be influenced by the purity of the compound, the heating rate, and the particle size. Therefore, crystalline Form D of the present invention may have DSC in the range of from about 159° C. to about 166° C.

An aspect of the present disclosure provides processes for preparing a crystalline form of bazedoxifene acetate designated as Form D, embodiments comprising at least one of the steps:

a) providing bazedoxifene free base in a suitable solvent;
b) adding a source of acetate ion; and
c) maintaining the mixture of step b) for a time and under conditions suitable for formation of crystalline Form D of bazedoxifene acetate.

Solvents employed for preparation of crystalline Form D of bazedoxifene acetate include, but are not limited to: an alcohol solvent, such as, for example, methanol, ethanol, or 2-propanol; an ether solvent, such as, for example, diisopropyl ether, methyl tert-butyl ether, diethyl ether, 1,4-dioxane, THF, or methyl THF; an ester solvent, such as, for example, ethyl acetate, isopropyl acetate, or t-butyl acetate; a ketone solvent such as acetone, methyl isobutyl ketone; a halogenated hydrocarbon solvent, such as, for example, dichloromethane, dichloroethane, chloroform, or the like; a hydrocarbon solvent, such as, for example, toluene, xylene, cyclohexane, or heptane; a nitrile solvent such as acetonitrile; a dipolar aprotic solvent such as dimethyl formamide, dimethylacetamide or the like; water; or any mixtures thereof.

A mixture comprising a bazedoxifene free base and a solvent may be obtained by providing bazedoxifene base in a suitable solvent, or such a mixture may be obtained directly from a reaction in which a bazedoxifene free base is synthesized. When a mixture is prepared by providing bazedoxifene free base in a suitable solvent, the bazedoxifene base may be in any form including any crystalline forms, amorphous forms, solvates, hydrates, crystalline anhydrates, or mixtures thereof.

In step b), sources of acetate ion include, but are not limited to, acetic acid. The source of acetate ion can be added to a mixture comprising bazedoxifene free base at temperatures such as about 0° C. to about 50° C., and the addition may take from about 30 minutes to about 5 hours or longer. The obtained reaction mixture may be further stirred until precipitation occurs.

In step c), the crystallization can be either initiated by cooling or by addition of a suitable anti-solvent or by both. An anti-solvent as used herein refers to a solvent in which crystalline Form D of bazedoxifene acetate is less soluble or poorly soluble and can be selected from the aforementioned list of solvents.

Suitable times for crystallization will vary and can be from about 10 minutes to about 1 hour, to about 24 hours, or longer. Suitable temperatures for crystallization include from about −10° C. to about 30° C. or from about 10° C. to about 20° C. Alternately, step-wise cooling can be done to ease the filtration by improving the morphology of crystalline particles. The amount of solvent per gram of crystalline bazedoxifene free base typically varies from about 20 mL to about 200 mL.

Undissolved particles from a mixture comprising bazedoxifene free base or acetate can be removed suitably by filtration, centrifugation, decantation, or other techniques, such as passing the solution through paper, glass fiber, a particulate bed, or a membrane material.

Further, the embodiment also includes the reverse mode of addition wherein a mixture comprising bazedoxifene free base is added to a mixture comprising source of acetate ion.

An another aspect of the present disclosure provides processes for preparing a crystalline form of bazedoxifene acetate designated as Form D, embodiments comprising at least one of the steps:

a) providing a mixture of bazedoxifene acetate in a suitable solvent;
b) adding seed crystals of crystalline bazedoxifene acetate Form D and a anti-solvent; and
c) isolating crystalline Form D of bazedoxifene acetate.

The mixture of step a) is a clear solution and it can be obtained by heating the reaction mixture to dissolution temperature that can be any temperature as long as the stability of the bazedoxifene acetate is not compromised and a substantially clear solution is obtained. For example, the dissolution temperature may range from about 20° C. to about the reflux temperature of the solvent. A mixture comprising bazedoxifene acetate and a solvent may be obtained by providing bazedoxifene acetate in a suitable solvent, or such a mixture may be obtained directly from a reaction in which bazedoxifene acetate is synthesized. When a mixture is prepared by providing bazedoxifene acetate in a suitable solvent, the bazedoxifene acetate may be in any form including any crystalline forms such as Form A, Form B and like, amorphous forms, solvates, hydrates, crystalline anhydrates, or mixtures thereof. Optionally before addition of seed crystals and anti-solvent, the volume of mixture of step a) can be reduced by evaporation of solvent under vacuum. The amount of seed crystals added in step b) can be 3-15% (w/w) to the starting material i.e. bazedoxifene acetate. Appropriate solvent and anti-solvent can be selected from the list mentioned above. Alternately, step-wise cooling can be done to ease the filtration by improving the morphology of crystalline particles. For example, the reaction mixture can first be cooled from about 30-35° C. to about 15-20° C. over a period of 1 hour followed by maintenance at 15-20° C. for another 1 hour and subsequent cooling to 0-5° C. over a period of about 30 minutes.

In both the aforementioned embodiments, once obtained, the crystals of bazedoxifene acetate Form D may be used as the nucleating agent or "seed" crystals for subsequent crystallizations of polymorphic Form D from solutions.

Microscopic observations show that the crystallization conditions strongly affect the particle size and morphology. Further, difference in particle morphology is not related to polymorphism. The crystalline bazedoxifene acetate Form D of the present application can have rod shaped morphology.

The purity of the product isolated at any stage of the process can further be increased by any purification technique, such as by recrystallizing or slurrying bazedoxifene free base or its acetate salt, or any other salt of bazedoxifene, in suitable solvents by processes known in the art. Suitable crystallization techniques include, but are not limited to: concentrating, cooling, stirring, or shaking a solution containing the compound, by adding anti-solvent, adding seed crystals, evaporation, flash evaporation, or the like. An anti-solvent as used herein refers to a solvent in which salt of bazedoxifene is less soluble or poorly soluble. The solvents that can be employed for crystallization include, but are not limited to: lower alcohols, such as methanol, ethanol, isopropyl alcohol; esters such as ethyl acetate, n-propyl acetate, or isopropyl acetate; ethers such as 1,4-dioxane or tetrahydrofuran; nitriles such as acetonitrile; or any mixtures thereof.

The compounds at any stage of the processes of the present disclosure may be recovered from a suspension or solution, using any of techniques such as decantation, filtration by gravity or by suction, centrifugation, slow evaporation, or the like, or any other suitable techniques. The solids that are isolated may carry a small proportion of occluded mother liquor containing a higher percentage of impurities. If desired, the solids may be washed with a solvent to wash out the mother liquor and/or impurities, and the resulting wet solids may optionally be dried. Evaporation, as used herein, refers to either partial distillation of solvent or almost complete distillation at atmospheric pressure or under reduced pressure. Flash evaporation as used herein refers to distilling of solvent by using a technique including, but not limited to, tray drying, spray-drying, fluidized bed drying, or thin film drying, under reduced pressure or at atmospheric pressure.

The recovered solid may be optionally dried. Drying may be carried out using a tray dryer, vacuum oven, air oven, fluidized bed dryer, spin flash dryer, flash dryer, or the like, at atmospheric pressure or under reduced pressure. The drying may be carried out at temperatures less than about 200° C., or about 20° C. to about 80° C., or about 30° C. to about 60° C., or any other suitable temperatures, at atmospheric pressure or under reduced pressure. The drying may be carried out for any desired times until the desired quality of product is achieved, such as about 30 minutes to about 5 hours, or about 1 to about 4 hours. Shorter or longer times also are useful.

In embodiments, the bazedoxifene salt has high purity, such as at least about 99%, at least about 99.5%, or at least about 99.9%, by weight as determined using high performance liquid chromatography (HPLC). Correspondingly, the level of impurities may be less than about 1%, less than about 0.5%, or less than about 0.1%, by weight, as determined using HPLC.

Aspects of the present disclosure include crystalline bazedoxifene and crystalline bazedoxifene acetate, formulated as: solid oral dosage forms, such as, for example, powders, granules, pellets, tablets, capsules; liquid oral dosage forms, such as, for example, syrups, suspensions, dispersions, emulsions; injectable preparations, such as, for example, solutions, dispersions, freeze dried compositions Immediate release compositions may be conventional, dispersible, chewable, mouth dissolving, or flash melt preparations. Modified release compositions may comprise hydrophilic and/or hydrophobic release rate controlling substances to form matrix and/or reservoir systems. The compositions may be prepared by techniques such as direct blending, dry granulation, wet granulation, extrusion and spheronization, etc. Compositions may be uncoated, film coated, sugar coated, powder coated, enteric coated, or modified release coated.

Pharmaceutical compositions of bazedoxifene or a salt thereof comprise one or more pharmaceutically acceptable excipients. Useful pharmaceutically acceptable excipients include, but are not limited to: diluents, such as, for example starches, pregelatinized starches, lactose, powdered celluloses, microcrystalline celluloses, dicalcium phosphate, tricalcium phosphate, mannitol, sorbitol, sugar, or the like; binders, such as, for example acacia, guar gum, tragacanth, gelatin, polyvinylpyrrolidones, hydroxypropyl celluloses, hydroxypropyl methylcelluloses, pregelatinized starches, or the like; disintegrants, such as, for example starches, sodium starch glycolate, pregelatinized starches, crospovidones, croscarmellose sodiums, colloidal silicon dioxides, or the like; lubricants, such as, for example stearic acid, magnesium stearate, zinc stearate, or the like; glidants, such as, for example colloidal silicon dioxides, or the like; solubility or wetting enhancers, such as, for example anionic, cationic, or neutral surfactants; complex forming agents, such as, for example various grades of cyclodextrins; release rate controlling agents, such as, for example hydroxypropyl celluloses, hydroxymethyl celluloses, hydroxypropyl methylcelluloses, ethyl celluloses, methyl celluloses, various grades of methyl methacrylates, waxes, or the like. Other pharmaceutically acceptable excipients include, but are not limited to, film formers, plasticizers, colorants, flavoring agents, sweeteners, viscosity enhancers, preservatives, antioxidants, or the like.

The polymorphic forms obtained by the present application, unless stated otherwise, were characterized by PXRD pattern, DSC curves, and TGA curves. PXRD data reported herein was obtained using CuKα radiation, having the wavelength 1.5418 Å and were obtained using a Bruker AXS D8 Advance Powder X-ray Diffractometer. DSC analysis was carried out in a DSC Q1000 instrument from TA Instruments with a ramp of 5° C./minute up to 250° C. TGA analysis was carried out in a TGA Q500 instrument with a ramp 10° C./minute up to 250° C. Crystalline forms are characterized by scattering techniques, e.g., x-ray diffraction powder pattern, by spectroscopic methods, e.g., infra-red, $^{13}C$ nuclear magnetic resonance spectroscopy, and by thermal techniques, e.g., differential scanning calorimetry or differential thermal analysis. The compound of this application is best characterized by the X-ray powder diffraction pattern determined in accordance with procedures that are known in the art. For a discussion of these techniques see J. Haleblain, J. Pharm. Sci. 1975 64:1269-1288, and J. Haleblain and W. McCrone, J. Pharm. Sci. 1969 58:911-929.

Generally, a diffraction angle (2θ) in powder X-ray diffractometry may have an error in the range of ±0.2°. Therefore, the aforementioned diffraction angle values should be understood as including values in the range of about ±0.2°. Accordingly, the present invention includes not only crystals whose peak diffraction angles in powder X-ray diffractometry completely coincide with each other, but also crystals whose peak diffraction angles coincide with each other with an error of about ±0.2°. Therefore, in the present specification, the phrase "having a diffraction peak at a diffraction angle (2θ±0.2°) of 7.9°" means "having a diffraction peak at a diffraction angle (2θ) of 7.7° to 8.1°". Although the intensities of peaks in the x-ray powder diffraction patterns of different batches of a compound may vary slightly, the peaks and the peak locations are characteristic for a specific polymorphic form. Alternatively, the term "about" means within an acceptable standard error of the mean, when considered by one of ordinary skill in the art. The relative intensities of the PXRD peaks can vary depending on the sample preparation technique, crystal size distribution, various filters used, the sample mounting procedure, and the particular instrument employed. Moreover, instrument variation and other factors can affect the 2-theta values. Therefore, the term "substantially" in the context of PXRD is meant to encompass that peak assignments can vary by plus or minus about 0.2 degree. Moreover, new peaks may be observed or existing peaks may disappear, depending on the type of the machine or the settings (for example, whether a Ni filter is used or not).

The $D_{10}$, $D_{50}$, and $D_{90}$ values are useful ways for indicating a particle size distribution. $D_{90}$ refers to at least 90 volume percent of the particles having a size smaller than the said value. Likewise, $D_{10}$ refers to 10 volume percent of the particles having a size smaller than the said value. $D_{50}$ refers to 50 volume percent of the particles having a size smaller than the said value. Methods for determining $D_{10}$, $D_{50}$, and $D_{90}$ include laser diffraction, such as using equipment from Malvern Instruments Ltd. of Malvern, Worcestershire, United Kingdom.

DEFINITIONS

The following definitions are used in connection with the compounds of the present application unless the context indicates otherwise. In general, the number of carbon atoms present in a given group is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions or the like. The term "reacting" is intended to represent bringing the chemical reactants together under condition such to cause the chemical reaction indicated to take place. Unless defined otherwise, technical and scientific terms used herein have the same meaning as commonly understood by one of ordinary skill in the art, to which this invention belongs. All percentages and ratios used herein are by weight of the total composition, unless the context indicates otherwise. All temperatures are in degrees Celsius unless specified otherwise. The present disclosure can comprise the components discussed in the present disclosure as well as other ingredients or elements described herein. As used herein, "comprising" means the elements recited, or their equivalents in structure or function, plus any other element or elements which are not recited. The terms "having" and "including" are also to be construed as open ended unless the context suggests otherwise. All ranges recited herein include the endpoints, including those that recite a range "between" two values. Terms such as "about," "generally," "substantially," or the like are to be construed as modifying a term or value such that it is not an absolute. Such terms will be defined by the circumstances and the terms that they modify, as those terms are understood by those of skill in the art. This includes, at very least, the degree of expected experimental error, technique error and instrument error for a given technique used to measure a value.

When a molecule or other material is identified herein as "pure", it generally means, unless specified otherwise, that the material has 99% purity or more, as determined by methods conventional in the art such as high performance liquid chromatography (HPLC) or spectroscopic methods. In general, this refers to purity with regard to unwanted residual solvents, reaction by-products, impurities, or unreacted starting materials. "Substantially pure" refers to the same as "pure" except that the lower limit is about 98% purity and, likewise, "essentially pure" means the same as "pure" except that the lower limit is about 95% purity.

An "alcohol solvent" is an organic solvent containing a carbon bound to a hydroxyl group. "Alcohol solvents" include but are not limited to methanol, ethanol, 2-nitroethanol, 2-fluoroethanol, 2,2,2-trifluoroethanol, hexafluoroisopropyl alcohol, ethylene glycol, 1-propanol, 2-propanol (isopropyl alcohol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, glycerol, $C_{1-6}$alcohols, and the like.

"Aromatic hydrocarbon solvent" refers to a liquid, unsaturated, cyclic, hydrocarbon containing one or more rings which has at least one 6-carbon ring containing three double bonds. It is capable of dissolving a solute to form a uniformly dispersed solution. Examples of an aromatic hydrocarbon solvent include, but are not limited to, benzene toluene, ethylbenzene, m-xylene, o-xylene, p-xylene, indane, naphthalene, tetralin, trimethylbenzene, chlorobenzene, fluorobenzene, trifluorotoluene, anisole, $C_6$-$C_{10}$aromatic hydrocarbons, or mixtures thereof.

A "dipolar aprotic solvent" has a dielectric constant greater than 15 and is at least one chosen from amide-based organic solvents, such as N,N-dimethylformamide (DMF), N,N-dimethylacetamide (DMA), N-methylpyrrolidone (NMP), formamide, acetamide, propanamide, hexamethyl phosphoramide (HMPA), and hexamethyl phosphorus triamide (HMPT); nitro-based organic solvents, such as nitromethane, nitroethane, nitropropane, and nitrobenzene; pyridine-based organic solvents, such as pyridine and picoline; sulfone-based solvents, such as dimethylsulfone, diethylsulfone, diisopropylsulfone, 2-methylsulfolane, 3-methylsulfolane, 2,4-dimethylsulfolane, 3,4-dimethy sulfolane, 3-sulfolene, and sulfolane; or sulfoxide-based solvents such as dimethylsulfoxide (DMSO).

An "ester solvent" is an organic solvent containing a carboxyl group —(C=O)—O— bonded to two other carbon atoms. "Ester solvents" include but are not limited to ethyl acetate, n-propyl acetate, n-butyl acetate, isobutyl acetate, t-butyl acetate, ethyl formate, methyl acetate, methyl propanoate, ethyl propanoate, methyl butanoate, ethyl butanoate, $C_{3-6}$esters, and the like.

An "ether solvent" is an organic solvent containing an oxygen atom —O— bonded to two other carbon atoms. "Ether solvents" include but are not limited to diethyl ether, diisopropyl ether, methyl t-butyl ether, glyme, diglyme, tetrahydrofuran, 1,4-dioxane, dibutyl ether, dimethylfuran, 2-methoxyethanol, 2-ethoxyethanol, anisole, $C_{2-6}$ethers, and the like.

A "ketone solvent" is an organic solvent containing a carbonyl group —(C=O)— bonded to two other carbon atoms. "Ketone solvents" include, but are not limited to, acetone, ethyl methyl ketone, diethyl ketone, methyl isobutyl ketone, $C_{3-6}$ketones, or the like.

"Halo" or "halogen" refers to fluorine, chlorine, bromine, or iodine.

A "halogenated hydrocarbon solvent" is an organic solvent containing a carbon bound to a halogen. "Halogenated hydrocarbon solvents" include, but are not limited to, dichloromethane, 1,2-dichloroethane, trichloroethylene, perchloroethylene, 1,1,1-trichloroethane, 1,1,2-trichloroethane, chloroform, carbon tetrachloride, or the like.

A "hydrocarbon solvent" refers to a liquid, saturated hydrocarbon, which may be linear, branched, or cyclic. It is capable of dissolving a solute to form a uniformly dispersed solution. Examples of a hydrocarbon solvent include, but are not limited to, n-pentane, isopentane, neopentane, n-hexane, isohexane, 3-methylpentane, 2,3-dimethylbutane, neohexane, n-heptane, isoheptane, 3-methylhexane, neoheptane, 2,3-dimethylpentane, 2,4-dimethylpentane, 3,3-dimethylpentane, 3-ethylpentane, 2,2,3-trimethylbutane, n-octane, isooctane, 3-methylheptane, neooctane, cyclohexane, methylcyclohexane, cycloheptane, $C_5$-$C_8$aliphatic hydrocarbons, and mixtures thereof.

A "nitrile solvent" is an organic solvent containing a cyano —(C≡N) bonded to another carbon atom. "Nitrile solvents" include, but are not limited to, acetonitrile, propionitrile, $C_{2-6}$nitriles, or the like.

Certain specific aspects and embodiments of the present disclosure will be explained in more detail with reference to the following examples, which are provided solely for purposes of illustration and are not to be construed as limiting the scope of the disclosure in any manner.

EXAMPLES

Example 1

Preparation of Crystalline Bazedoxifene Free Base Form A

Bazedoxifene hydrochloride (5 g), dichloromethane (75 mL), and water (50 mL) are mixed and triethylamine (4 mL) is slowly added to obtain a pH range of 9.5-10.5 of the aqueous phase. The layers are separated and the aqueous layer is extracted with dichloromethane (2×25 mL). The organic layers are combined followed by addition of water (50 mL), at which point pH of the aqueous phase is about 10.4. To this mixture, a solution of 5% acetic acid (75 mL) is slowly added until the pH is about 9, at which point a crystalline solid forms. The solid is collected by filtration, washed with dichloromethane (25 mL), and dried under vacuum at 50° C. to afford crystalline bazedoxifene free base in 73.27% yield (HPLC purity 99.67%).

Example 2

Preparation of Crystalline Bazedoxifene Free Base Form A

Bazedoxifene acetate (15 g) and dimethylformamide (75 mL) are mixed and heated to 70-75° C. to produce a clear solution, followed by filtration to make it particle free. To the filtrate, toluene (1000 mL), morpholine (1 mL), and water (500 mL) are added and the mixture is cooled to 25-30° C. and stirred overnight. The solid that forms is collected by filtration, washed with toluene (20 mL), and dried under vacuum at 70° C. for 5 hours to afford 10 g of crystalline bazedoxifene free base Form A.

Example 3

Preparation of Crystalline Bazedoxifene Free Base Form A

Bazedoxifene acetate (2 g) and dimethylformamide (10 mL) are mixed and heated to 70-75° C. to produce a clear solution, followed by filtration. To the filtrate, toluene (400 mL), morpholine (1 mL), and water (100 mL) are added and the mixture is cooled to 0-10° C. and stirred overnight. The solid that forms is collected by filtration, washed with toluene (20 mL), and dried under vacuum below 80° C. for about 5 hours to afford crystalline bazedoxifene free base Form A (HPLC purity 99.2%, moisture content=0.32%).

Example 4

Preparation of Crystalline Bazedoxifene Free Base Form A

Bazedoxifene acetate (47 g) and dimethylformamide (235 mL) are mixed and heated to 80° C. to produce a clear solution, followed by filtration. To the filtrate, toluene (2700 mL), morpholine (3.0 mL), and water (1810 mL) are added and the mixture is stirred overnight at room temperature. The solid is collected by filtration, washed with toluene (70 mL) and water (70 mL), then dried under vacuum below 80° C. for about 6-8 hours to afford Form A of crystalline bazedoxifene free base: $D_{90}$=49.80 microns; $D_{10}$=3.61 microns, $D_{50}$=25.30 microns. The material is subjected to micronization under nitrogen atmosphere with a pressure of 4 kg/cm² to afford the particles with $D_{90}$=6.04 microns; $D_{10}$=0.89 microns, $D_{50}$=2.37 microns.

Example 5

Preparation of Crystalline Bazedoxifene Free Base Form A

Bazedoxifene hydrochloride (1 g) and dimethylsulfoxide (10 mL) are mixed and heated to 60-70° C. to produce a clear solution, followed by filtration. To the filtrate, toluene (50 mL), morpholine (1 mL), and water (30 mL) are added and the mixture is stirred at room temperature for 12-24 hours. The solid so formed is collected by filtration, washed with toluene (5 mL), water (5 mL) and dried under vacuum below 80° C. for about 7 hours to afford 800 mg of crystalline bazedoxifene free base Form A.

Example 6

Preparation of Crystalline Bazedoxifene Free Base Form A

Bazedoxifene hydrochloride (2 g), ethyl acetate (20 mL) and acetone (30 mL) are mixed. To the mixture, 10% aqueous sodium hydroxide solution (5 mL) is drop-wise added followed by addition of water (120 mL) and stirring is continued at room temperature for solid formation. The solid so formed is collected by filtration, washed with water (20 mL) and dried under vacuum below 75° C. for about 6-8 hours to afford 1.8 g of crystalline bazedoxifene free base Form A.

Example 7

Preparation of Crystalline Bazedoxifene Free Base Form A

Bazedoxifene hydrochloride (2 g) and dimethylsulfoxide (16 mL) are mixed and heated to 60-70° C. to produce a clear solution, followed by cooling to room temperature and filtration to make it particle free. To the filtrate, toluene (100 mL), aqueous sodium carbonate solution (10%, 5 mL) and water (50 mL) are added and the mixture is stirred at room temperature for solid formation. The solid so formed is collected by filtration, washed with toluene (5 mL), water (5 mL) and dried under vacuum below 80° C. to afford 1.7 g of crystalline bazedoxifene free base Form A.

Example 8

Preparation of Crystalline Bazedoxifene Free Base Form A

Bazedoxifene acetate (3 g) and dimethylsulfoxide (15 mL) are mixed and heated to 60-70° C. to produce a clear solution, followed by cooling to room temperature and filtration to make it particle free. To the filtrate, toluene (150 mL), 10% aqueous sodium carbonate solution (5 mL) and water (75 mL) are added and the mixture is stirred at room temperature for solid formation. The solid so formed is collected by filtration, washed with toluene (6 mL), water (6 mL) and dried under vacuum below 80° C. for about 7 hours to afford 2.5 g of crystalline bazedoxifene free base Form A.

Example 9

Preparation of Crystalline Bazedoxifene Acetate Form D

Bazedoxifene free base (400 mg) and methyl tert-butyl ether (30 mL) are mixed and stirred for about 10 minutes. Acetic acid (0.17 g) is added slowly through a dropper and the mixture is stirred overnight for solid formation. The solid is collected by filtration to afford 250 mg of crystalline bazedoxifene acetate Form D.

Example 10

Preparation of Crystalline Bazedoxifene Acetate Form D

Bazedoxifene free base (400 mg) and toluene (30 mL) are mixed and stirred for about 10 minutes. Acetic acid (0.17 g) is added slowly through a dropper and the mixture stirred overnight for solid formation. The solid is collected by filtration to afford 200 mg of crystalline bazedoxifene acetate Form D.

Example 11

Preparation of Crystalline Bazedoxifene Acetate Form D

Bazedoxifene free base (500 mg) and ethanol (10 mL) are mixed and stirred for about 10 minutes. Acetic acid (2 mL) is added slowly through a dropper and the mixture is stirred for 10 minutes at room temperature to produce a clear solution. Diisopropyl ether (30 mL) is added and the mixture is stirred overnight for solid formation. The solid is collected by filtration and washed sequentially with diisopropyl ether (5 mL) and water (5 mL), then is suction dried for 5 minutes. The obtained wet solid is further dried under vacuum at 70° C. for about 4-5 hours to afford 420 mg (85% yield) of crystalline bazedoxifene acetate Form D.

Example 12

Preparation of Crystalline Bazedoxifene Acetate Form D

Bazedoxifene free base (1 g) and ethanol (10 mL) are mixed and heated to 60° C. to produce a clear solution, which is then filtered. The filtrate is cooled to 25-35° C. and acetic acid (4 mL) is slowly added at the same temperature. The mixture is cooled to 10-15° C., followed by addition of diisopropyl ether (5 mL) and seed crystals (20 mg, obtained from a previous example), and then additional diisopropyl ether (55 mL). The mixture is stirred for solid formation. The solid is collected by filtration and sequentially washed with diisopropyl ether (10 mL) and water (5 mL), then is suction dried for 5 minutes. The wet solid is dried under vacuum at 70° C. for about 4-5 hours to afford 900 mg (about 80% yield) of crystalline bazedoxifene acetate Form D.

Example 13

Preparation of Crystalline Bazedoxifene Acetate Form D

Bazedoxifene free base (2 g) and acetone (20 mL) are mixed and heated to 45-50° C. to produce a clear solution, which is filtered. The filtrate is cooled to 25-35° C. and seed crystals (20 mg) are added, followed by drop-wise addition of acetic acid (0.26 g). n-Heptane (50 mL) is added drop-wise over 30 minutes. The formed solid is collected by filtration, sequentially washed with n-heptane (10 mL), and then suction dried for 5 minutes. The wet solid is dried under vacuum at 70° C. for about 4-5 hours to afford 1.5 g of crystalline bazedoxifene acetate Form D.

Example 14

Preparation of Crystalline Bazedoxifene Acetate Form D

Bazedoxifene free base (2 g) and ethanol (4 mL) are mixed and stirred at 25-30° C. Acetic acid (2 mL) is added drop-wise and stirring is continued at the same temperature for 10 minutes. The mixture is cooled to 10-15° C., followed by drop-wise addition of diisopropyl ether (60 mL) and seed crystals (40 mg). The mixture is stirred at the same temperature for 10 minutes and the solid is collected by filtration, sequentially washed with diisopropyl ether (20 mL) and water (5 mL), and suction dried for 5 minutes. The obtained wet solid is dried under vacuum at 70° C. for about 4-5 hours to afford 1.7 g of crystalline bazedoxifene acetate Form D. HPLC purity=99.46%, moisture content=0.61%.

Example 15

Preparation of Crystalline Bazedoxifene Acetate Form D

Bazedoxifene free base (500 mg) and acetone (8 mL) are mixed and stirred at 50-60° C. to make a clear solution. The solution is filtered followed by addition of seed crystals of bazedoxifene acetate (10 mg) and drop-wise addition of acetic acid (0.12 mL). To the mixture, heptane (40 mL) is added over a period of 10 and mixture is stirred for another 10-15 minutes. The solid so obtained is collected by filtration, washed with heptane (10 mL), and dried by suction. The obtained wet solid is then further dried under vacuum at 65-70° C. for about 6-8 hours to afford 400 mg of crystalline bazedoxifene acetate Form D.

Example 16

Preparation of Crystalline Bazedoxifene Acetate Form D

Bazedoxifene free base (700 mg) and acetone (8 mL) are mixed and stirred at 45-55° C. to make a clear solution. The solution is filtered followed by addition of seed crystals of bazedoxifene acetate (20 mg) and drop-wise addition of a mixture of acetic acid (0.1 mL) in acetone (1 mL) at room temperature. To the mixture, heptane (40 mL) is added over a period of 15-30 minutes and mixture is stirred for another 30 minutes. The solid so obtained is collected by filtration, washed with heptane (5 mL), and dried by suction. The obtained wet solid is then further dried under vacuum at below 70° C. for about 6-8 hours to afford 850 mg of crystalline bazedoxifene acetate Form D.

Example 17

Preparation of Crystalline Bazedoxifene Acetate Form D

Bazedoxifene free base (3 g) and acetone (30 mL) are mixed and stirred at 50-55° C. to make a clear solution. Then acetic acid (0.4 mL) and seed crystals of bazedoxifene acetate (60 mg) are added to the solution under continuous stirring at room temperature. To the mixture, heptane (60 mL) is added over a period of 5-10 minutes and mixture is stirred for another 10 minutes. The solid so obtained is collected by filtration and washed with heptane (15 mL) and dried under vacuum at below 80° C. for about 6-8 hours to afford 2.0 g of crystalline bazedoxifene acetate Form D. $D_{90}$=106.3 microns, $D_{10}$=5.80 microns, $D_{50}$=50.625 microns.

Example 18

Preparation of Crystalline Bazedoxifene Acetate Form D

Bazedoxifene free base (18 g) and acetone (162 mL) are mixed and stirred at 45-55° C. to make a clear solution. The said solution is cooled to room temperature and filtered to make particle free. To the filtrate, seed crystals of bazedoxifene acetate (360 mg) are added at room temperature and mixture is cooled to 15-20° C. followed by addition of a solution of acetic acid (2.34 g) in acetone (18 mL) at the same temperature. To the mixture, heptane (486 mL) is added over a period of 5-10 minutes and mixture is stirred at 15-20° C. for solid formation. The solid so obtained is collected by filtration and washed with heptane (50 mL) and dried under vacuum at below 80° C. to afford 17.80 g of crystalline bazedoxifene acetate Form D. $D_{90}$=76.17 microns; $D_{10}$=3.58 microns, $D_{50}$=33.59 microns. The material is subjected to micronization under nitrogen atmosphere with a pressure of 4 kg/cm² to afford the particles with $D_{90}$=12.32 microns; $D_{10}$=1.11 microns, $D_{50}$=4.19 microns.

Example 19

Preparation of Crystalline Bazedoxifene Acetate Form D

Amorphous bazedoxifene acetate Form C, (500 mg) and acetone (30 mL) are charged are mixed and stirred at 45-55° C. temperature to make a clear solution. The solution is filtered followed by partial evaporation (about 90%) of solvent from the filtrate. The remaining mixture in the flask is subjected to cooling to 15-30° C. and seed crystals of bazedoxifene acetate (10 mg) are added to it. Then slowly n-heptane (30 mL) is added to the above mixture and reaction mixture is stirred for precipitate formation. The solid is collected by filtration and washed with n-heptane (5 mL) to afford the title compound.

Example 20

Preparation of Crystalline Bazedoxifene Acetate Form D

Crystalline bazedoxifene acetate Form A (1 g) is dissolved in acetone (30 mL) at reflux temperature to make a clear solution. The solution is filtered followed by addition of seed crystals of bazedoxifene acetate (20 mg). Then slowly n-heptane (30 mL) is added to the above mixture and reaction mixture is stirred for precipitate formation for about 10 minutes. The solid is collected by filtration, washed with n-heptane (10 mL), and dried by suction to afford the title compound.

Example 21

Preparation of Crystalline Bazedoxifene Acetate Form D

Crystalline bazedoxifene acetate Form B (1 g) is dissolved in acetone at 50-55° C. temperature to make a clear solution. The solution is then subjected to about 92% evaporation of solvent from the mixture under vacuum at 40-45° C. The remaining mixture is cooled to room temperature and then filtered to make it particle free and subsequently further cooled to 15-20° C. followed by addition of seed crystals of bazedoxifene acetate (20 mg) at the same temperature. Then slowly n-heptane (30 mL) is added to the above mixture at the same temperature and reaction mixture is stirred for precipitate formation for about 60 minutes. The solid is collected by filtration and washed with n-heptane (5 mL) to afford the title compound.

Example 22

Preparation of Bazedoxifene Free Base

A mixture of 1-(4-(2-(azepan-1-yl)ethoxy)benzyl)-5-(benzyloxy)-2-(4-benzyloxy)phenyl)-3-methyl-1H-indole (15 g) and ethyl acetate (150 mL) is heated to 40° C. to produce a clear solution, then 10% palladium on carbon (3 g) is added and the mixture is stirred under 10 Kg/cm² hydrogen pressure at 45-50° C. until completion of the reaction (about 2 hours), as verified using TLC. The mixture is cooled to room temperature, filtered, and the collected solid washed with ethyl acetate (30 mL). The filtrate is used further treatments.

Example 23

Preparation of Crystalline Bazedoxifene Acetate Form D

To the ethyl acetate layer containing bazedoxifene free base (15 mL, from example no. 22), seed crystals of bazedoxifene acetate (20 mg), and acetic acid (0.13 g) are added and the mixture is stirred for 5-10 minutes at room temperature. The solid is collected by filtration, washed with ethyl acetate (10 mL), and then is suction dried for 5 minutes to afford the title compound.

Example 24

Preparation of Crystalline Bazedoxifene Free Base Form A

To the ethyl acetate layer containing bazedoxifene free base (15 mL, from example no. 22), seed crystals of crystalline bazedoxifene free base (20 mg) are added and the mixture is stirred for 10-15 minutes at room temperature. The solid is collected by filtration and washed with ethyl acetate (5 mL), and then is suction dried for 5 minutes to afford the title compound.

Example 25

Preparation of Crystalline Bazedoxifene Free Base Form A

The ethyl acetate layer containing bazedoxifene free base (15 mL, from example no. 22) is subjected to complete evaporation under vacuum at 55-60° C. to afford the title compound.

Example 26

Purification of 1-(4-(2-(Azepan-1-yl)Ethoxy)Benzyl)-5-(Benzyloxy)-2-(4-Benzyloxy)Phenyl)-3-Methyl-1H-Indole (dibenzylated bazedoxifene)

A mixture of 1-(4-(2-(azepan-1-yl)ethoxy)benzyl)-5-(benzyloxy)-2-(4-benzyloxy)phenyl)-3-methyl-1H-indole (40 g) and ethyl acetate (400 mL) is heated to 45-50° C. to produce a clear solution, then acetic acid (5.5 g) is added and the mixture is stirred for 15-30 minutes at the same temperature. The reaction mixture is then cooled to 0-5° C. and stirred for solid separation. The solid so obtained is collected by filtration and washed with chilled ethyl acetate (40 mL). The solid is then taken up in 10% aqueous sodium bicarbonate (100 mL) followed by addition of ethyl acetate (200 mL). The organic layer is separated and subjected to complete evaporation under vacuum to afford the title compound of enhanced purity.

Example 27

Preparation of Crystalline Bazedoxifene Acetate Form D

Crystalline bazedoxifene free base (60 g) is charged in a mixture of methanol (720 mL) and isopropyl alcohol (480 mL) and heated at reflux temperature to make a clear solution. The solution is filtered and cooled to 25-30° C. followed by addition of acetic acid (9.94 g). The reaction mixture is stirred for 15-30 minutes and subsequently seed crystals of Form D (3 g) are added and further the mixture is stirred at the same temperature for about 30 minutes. The reaction mixture is then cooled to 0-5° C. over a period of 1 hour and stirred at the same temperature for 15-30 minutes. The solid is collected by filtration and washed with pre-cooled mixture of methanol (72 mL) and isopropyl alcohol (48 mL), and dried under vacuum at about 90° C. for 5-8 hours to afford the title compound in about 87% yield.

Example 28

Preparation of Crystalline Bazedoxifene Acetate Form D

Crystalline bazedoxifene free base (5 g) is charged in methanol (100 mL) heated at reflux temperature to make a clear solution. The solution is filtered and cooled to 25-30° C. followed by addition of acetic acid (0.82 g). The reaction mixture is stirred for about 1 hour. In a separate flask, slurry of crystalline Form D of bazedoxifene acetate is prepared by providing seed of Form D (250 mg) in methanol (5 mL). The said seed slurry is added to the previous reaction mixture and further it is cooled to 10-15° C. in a period of 30 minutes followed by addition of isopropyl alcohol in a period of 2 hours. The reaction mixture is further cooled to 0-5° C. and maintained at same temperature for 30-45 minutes. The solid is collected by filtration and sequentially washed with isopropyl alcohol (5 mL) and methanol (5 mL), and dried under vacuum at about 90° C. to afford the title compound.

Example 29

Preparation of Crystalline Bazedoxifene Acetate Form D

Crystalline bazedoxifene free base (20 g) is charged in a mixture of methanol (200 mL) and isopropyl alcohol (200 mL) and heated at reflux temperature to make a clear solution. The solution is filtered and cooled to 25-30° C. followed by addition of acetic acid (3.31 g). The reaction mixture is stirred for 15-30 minutes and subsequently seed crystals of Form D (1 g) are added and further the mixture is stirred at the same temperature for about 30 minutes. The reaction mixture is then cooled to 0-5° C. over a period of 30 minutes and stirred at the same temperature for 15-30 minutes. The solid is collected by filtration and washed with pre-cooled mixture of methanol (10 mL) and isopropyl alcohol (10 mL), and dried under vacuum at about 90° C. for 5-8 hours to afford the title compound.

Example 30

Preparation of Crystalline Bazedoxifene Acetate Form D

Crystalline bazedoxifene free base (5 g) is charged in methanol (100 mL) heated at reflux temperature to make a clear solution. The solution is filtered and cooled to 25-30° C. followed by addition of acetic acid (0.82 g). The reaction mixture is stirred for ~1 hour followed by addition of seed crystals of Form D (250 mg). The reaction mixture is allowed to cool to 0-5° C. at which point water (200 mL) is slowly added over a period of 2 hours. The reaction mixture is maintained under stirring for another 1 hour at 0-5° C. The solid is collected by filtration and washed with water (10 mL), and dried under vacuum at about 90° C. to afford the title compound.

Example 31

Preparation of Crystalline Bazedoxifene Acetate Form D

Crystalline bazedoxifene free base (5 g) is charged in methanol (100 mL) heated at reflux temperature to make a clear solution. The solution is filtered and cooled to 25-30° C. followed by addition of acetic acid (0.82 g). The reaction mixture is stirred for about 1 hour followed by addition of seed slurry of Form D (providing 250 mg of Form D crystals in 5 mL of methanol). The reaction mixture is allowed to cool to 0-5° C. in 30 minutes and maintained at the same temperature for another 30-40 minutes. The solid is collected by filtration and washed with water (10 mL), and dried under vacuum at about 90° C. to afford the title compound.

Example 32

Preparation of Crystalline Bazedoxifene Free Base Form A

Bazedoxifene hydrochloride (20 g) and dimethylformamide (200 mL) are charged into a round bottomed flask and stirred for 10-15 minutes. To the reaction mixture, triethylamine (8 mL) and toluene (400 mL) are added and the mixture is stirred at room temperature for 10-20 minutes. Then two lots of water (40 mL and 860 mL) are sequentially added with intermittent stirring for 10-20 minutes and finally the reaction mixture is stirred for 5-6 hours at room temperature. The reaction mixture is then cooled to 7.5-12.5° C. and stirred at the same temperature for another 3-4 hours. The solid formed is collected by filtration, washed with water (40 mL), toluene (40 mL) and dried under vacuum below 50° C. to afford 16.2 g of crystalline bazedoxifene free base Form A of 99.79% HPLC purity.

Example 33

Preparation of Crystalline Bazedoxifene Free Base Form A

Bazedoxifene hydrochloride (5 g) and dimethylformamide (50 mL) are charged into a round bottomed flask, heated to 70-75° C. and stirred for clear solution. The reaction mixture is cooled to 25-35° C. followed by addition of triethylamine (2 mL), toluene (150 mL) and water (150 mL) and subsequently the mixture is stirred at room temperature for 5-6 hours. The solid formed is collected by filtration, washed with water (10 mL), toluene (10 mL) and dried under vacuum below 50° C. to afford crystalline bazedoxifene free base Form A of 99.72% HPLC purity.

Example 34

Preparation of Crystalline Bazedoxifene Free Base Form A

Bazedoxifene hydrochloride (10 g) and dimethylformamide (100 mL) are charged into a round bottomed flask, heated to about 70-75° C. and stirred for clear solution. The reaction mixture is cooled to 25-35° C. followed by addition of triethylamine (4 mL), toluene (200 mL) and water (450 mL) and subsequently the mixture is stirred at room temperature for 5-6 hours. The reaction mixture is cooled to 7.5-12.5° C. and stirred at same temperature for 3-4 hours. The solid formed is collected by filtration, washed with water (20 mL), toluene (20 mL) and dried under vacuum below 50° C. to afford crystalline bazedoxifene free base Form A of 99.74% HPLC purity.

Example 35

Preparation of Crystalline Bazedoxifene Free Base Form A

Bazedoxifene hydrochloride (50 g) and dimethylformamide (400 mL) are charged into a round bottomed flask, heated to about 70-75° C. and stirred for clear solution. The reaction mixture is cooled to 25-35° C. followed by addition of toluene (2500 mL), morpholine (50 mL) and water (1500 mL) and subsequently the mixture is stirred at room temperature for 12-24 hours. The solid formed is collected by filtration, washed with water (100 mL), toluene (100 mL) and dried under vacuum below 70° C. to afford crystalline bazedoxifene free base Form A of 99.65% HPLC purity.

Example 36

Preparation of Crystalline Bazedoxifene Acetate Form D

Crystalline bazedoxifene free base (35 g) is charged in a mixture of methanol (420 mL) and isopropyl alcohol (280 mL) and heated at reflux temperature to make a clear solution. The solution is filtered and cooled to 25-30° C. followed by addition of acetic acid (5.8 g) and then seed crystals of Form D (1.75 g). Further the mixture is stirred at the same temperature for about 20 minutes. The reaction mixture is then cooled to 0-5° C. over a period of about 30 minutes and stirred at the same temperature for 15-30 minutes. The solid is collected by filtration, washed with methanol (70 mL), and dried under vacuum at about 80° C. for 5-8 hours to afford the title compound.

Example 37

Preparation of Crystalline Bazedoxifene Acetate Form D

Acetic acid (0.764 g) is charged in a mixture of ethyl acetate (35 mL) and ethanol (15 mL) and reaction mixture is cooled to −5 to −10° C. In a separate flask, crystalline bazedoxifene free base is dissolved in mixture of ethyl acetate (35 mL) and ethanol (15 mL) and the said mixture is added to the previous reaction mixture of acetic acid at −5 to −10° C. The mixture is stirred at same temperature for about 24 hours. The solid is collected by filtration and dried under vacuum at about 50° C. for 3 hours to afford the title compound.

Example 38

Preparation of Crystalline Bazedoxifene Acetate Form D

Crystalline bazedoxifene free base (35 g) is charged in a mixture of methanol (420 mL) and isopropyl alcohol (280 mL) and heated to reflux temperature to make a clear solution. The solution is filtered, cooled to about 38° C., followed by addition of acetic acid (5.8 g), and then seed crystals of Form D (1.75 g) are added. Then the mixture is allowed to cool to 0° C. over a period of about 2 hours. The solid is collected by filtration, washed with precooled methanol (70 mL), and dried under vacuum at about 65° C. for 5 hours to afford the title compound having HPLC Purity of 99.70%. The obtained compound has PSD as $D_{90}$=61.97 microns, $D_{50}$=13.52 microns and $D_{10}$=3.45 microns and specific surface area of 1.72 m$^2$/g. The sample is subjected to micronization to afford compound having $D_{90}$=5.97 microns, $D_{50}$=2.90 microns and $D_{10}$=1.11 microns and specific surface area of 4.56 m$^2$/g.

Example 39

Preparation of Crystalline Bazedoxifene Acetate Form D

Crystalline bazedoxifene free base (10 g) is charged in a mixture of methanol (120 mL) and isopropyl alcohol (50 mL) and heated to reflux temperature to make a clear solution. The solution is filtered and cooled to about 27° C. over a period of 15 minutes followed by addition of acetic acid (1.65 g) and then seed crystals of Form D (0.5 g). Then the mixture is further allowed to cool to 0° C. over a period of about 2 hours. The reaction mixture is maintained at the same temperature for 1 hour and the solid is collected by filtration, washed with precooled methanol (20 mL), and dried under vacuum at about 70° C. for about 6 hours to afford the title compound having HPLC Purity of 99.84%.

Example 40

Preparation of Crystalline Bazedoxifene Acetate Form D

Crystalline bazedoxifene free base (1.7 Kg) is charged in a mixture of methanol (20.4 L) and isopropyl alcohol (13.6 L) and heated to reflux temperature to make a clear solution and stirred at same for 15-30 minutes. The solution is filtered and subsequently cooled to about 25-30° C. over a period of 10 minutes followed by addition of acetic acid (0.28 Kg) and seed crystals of Form D (85 g). Then the mixture is further allowed to cool to 0-5° C. over a period of about 20 minutes. The reaction mixture is maintained at the same temperature for 30-60 minutes and the solid is collected by filtration, washed with pre-cooled methanol (3.4 L), and dried under vacuum at about 60-65° C. to afford the title compound.

Example 41

Preparation of Crystalline Bazedoxifene Free Base Form A

Bazedoxifene hydrochloride (3 Kg), dimethylformamide (30 L), triethylamine (1.2 L), and toluene (60 L) are charged in a reactor and stirred for 10-20 minutes at 25-35° C. Then two lots of water (6 L and 129 L) are sequentially added with intermittent stirring for 10-20 minutes and finally the reaction mixture is stirred for 5-6 hours at 25-35° C. The reaction mixture is then cooled to 7.5-12.5° C. and stirred at the same temperature for another 3-4 hours. The solid formed is collected by filtration, washed with water (4 L), with toluene (4 L), and dried under vacuum at about 50° C. for 8 hours to afford crystalline bazedoxifene free base Form A in about 88% yield.

Example 42

Preparation of Crystalline Bazedoxifene Acetate Form D

Figure 8:
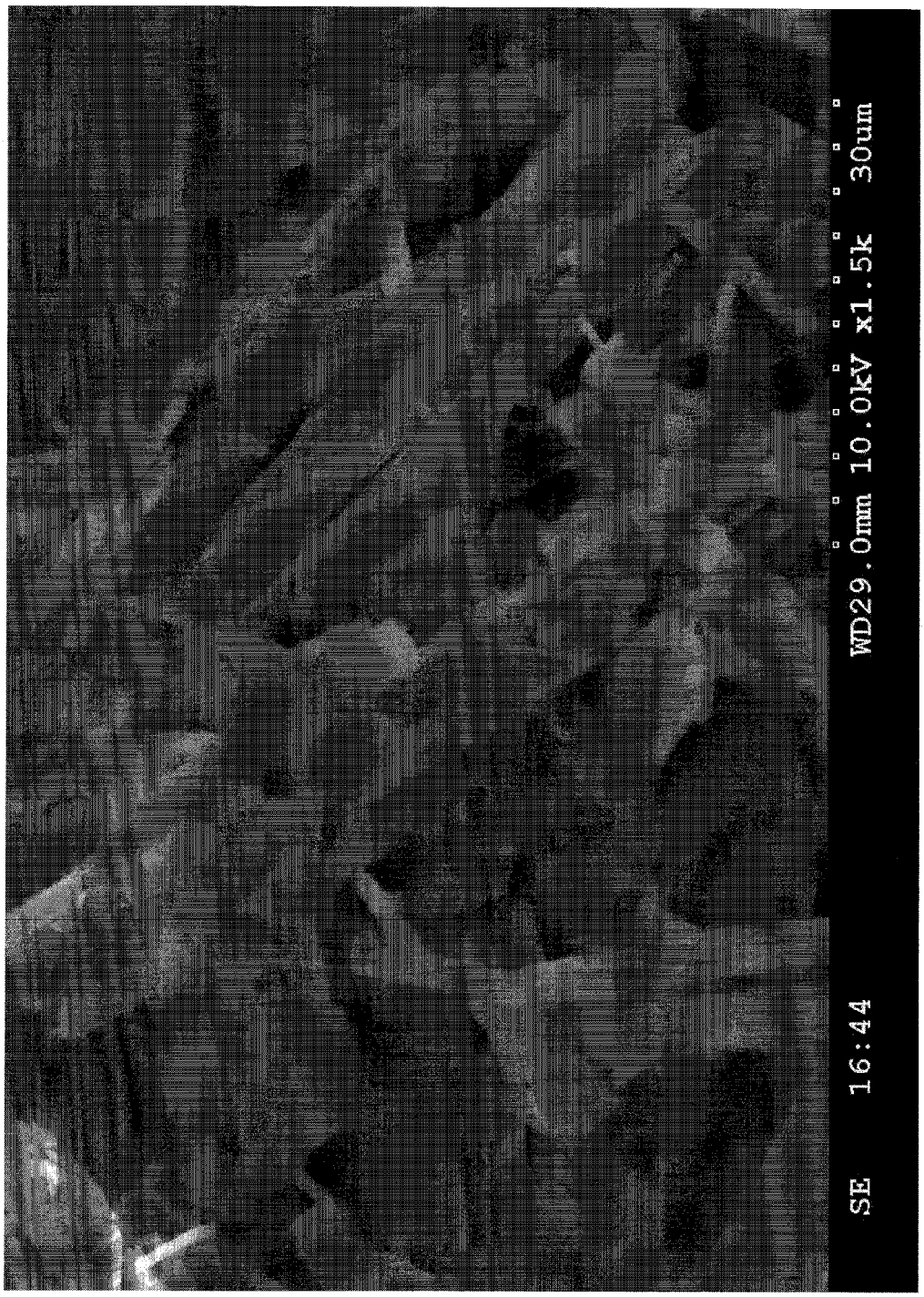
FIG. 8 is a SEM image of crystalline bazedoxifene acetate Form D obtained in accordance with Example 42

Crystalline bazedoxifene free base (15 g) is charged in a mixture of methanol (180 mL) and isopropyl alcohol (120 mL) and heated to reflux temperature to make a clear solution. The solution is filtered and cooled to about 25-30° C. over a period of 15 minutes followed by addition of acetic acid (1.91 g) and then seed crystals of Form D (0.75 g). Then the mixture is maintained at same temperature for about 20 minutes and then allowed to cool to 0° C. over a period of about 30 minutes. The solid is collected by filtration and dried under vacuum at about 80° C. for about 5 hours to afford the title compound having HPLC Purity of 99.80%. The obtained sample is analyzed by Scanning Electron Microscope and the image is depicted in FIG. 8.

Throughout this application, various publications are referenced. The disclosures of these publications in their entireties are hereby incorporated by reference into this application in order to more fully describe the state of the art as known to those skilled therein as of the date of the invention described and claimed herein.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. A Crystalline form of bazedoxifene acetate having a powder X-ray diffraction comprising characteristics peaks at 2θ values of about 5.9, 7.8, 11.7 and 17.7 degrees.

Figure 4:
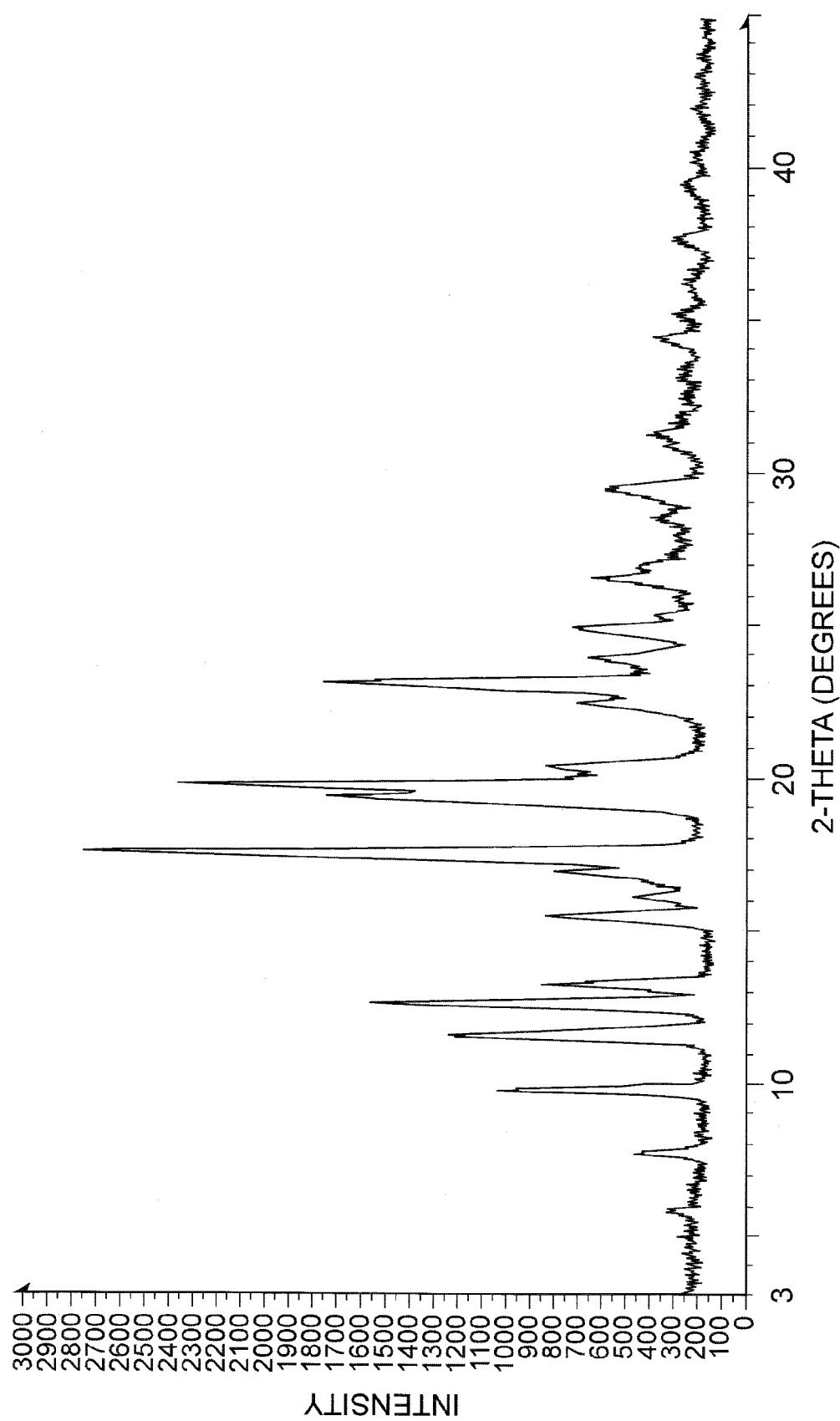
FIG. 4 is a PXRD pattern of crystalline bazedoxifene acetate Form D obtained in accordance with Example 14
Figure 5:
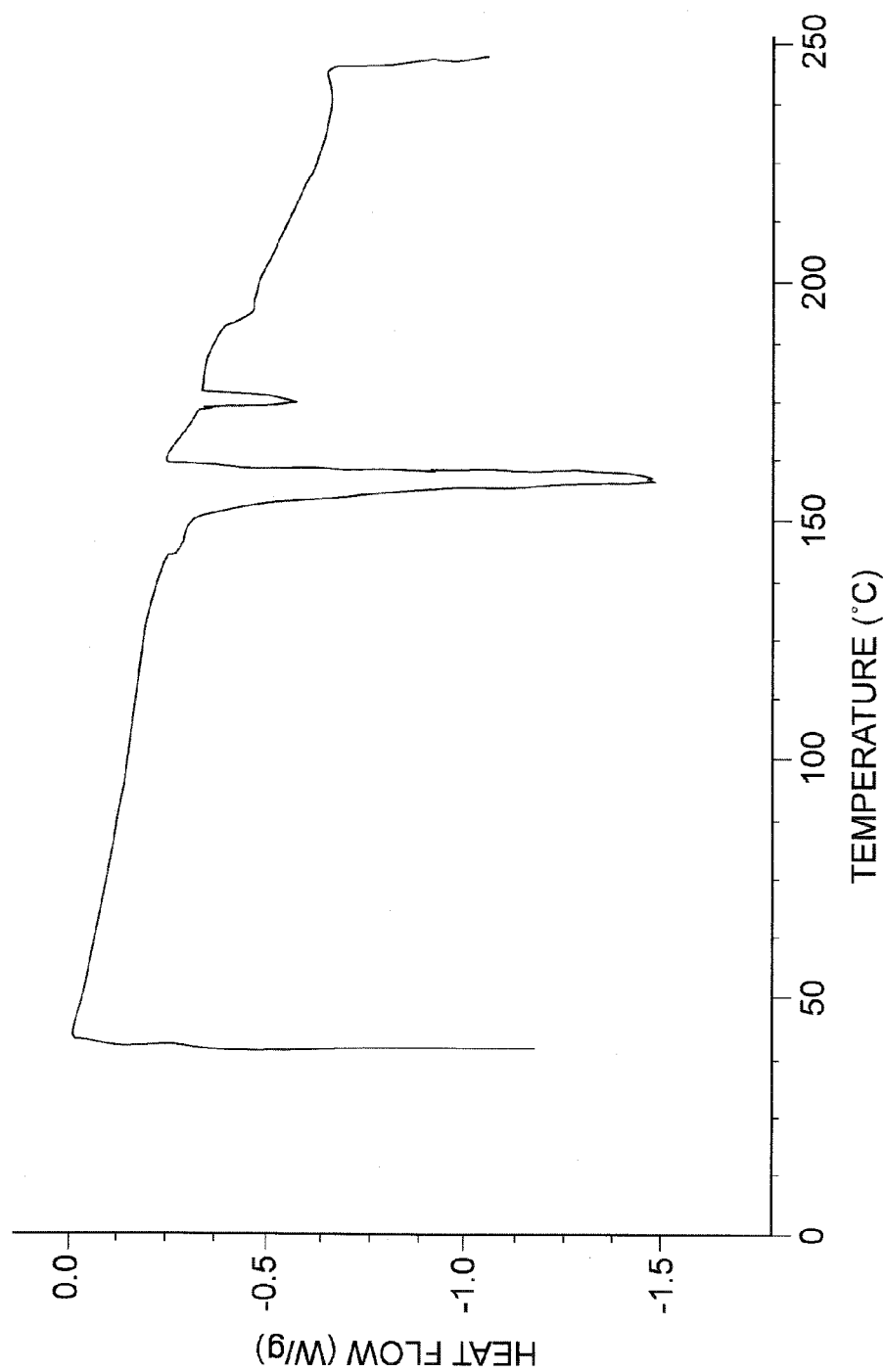
FIG. 5 is a DSC curve of crystalline bazedoxifene acetate Form D obtained in accordance with Example 14
Figure 6:
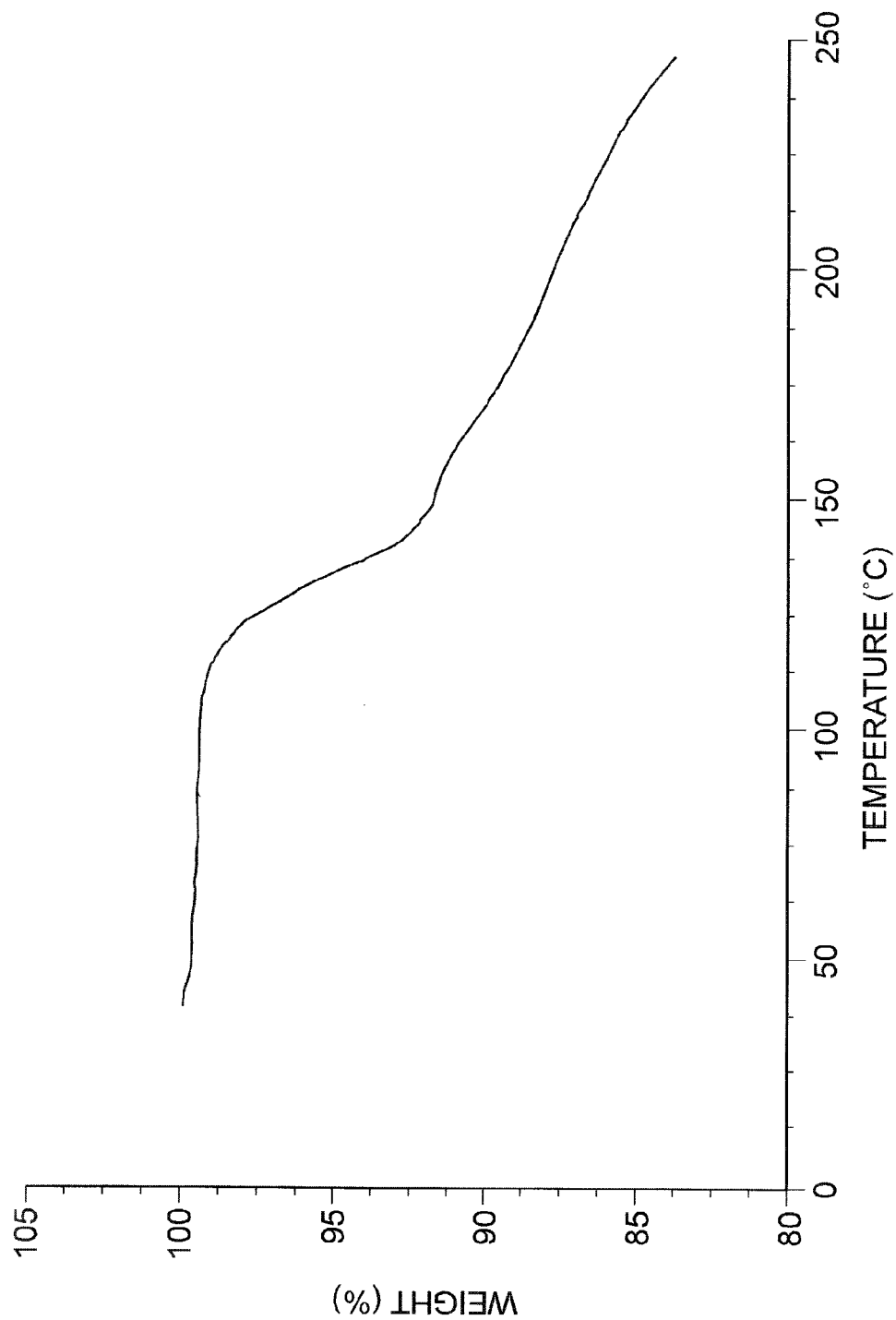
FIG. 6 is a TGA curve of crystalline bazedoxifene acetate Form D obtained in accordance with Example 14
Figure 7:
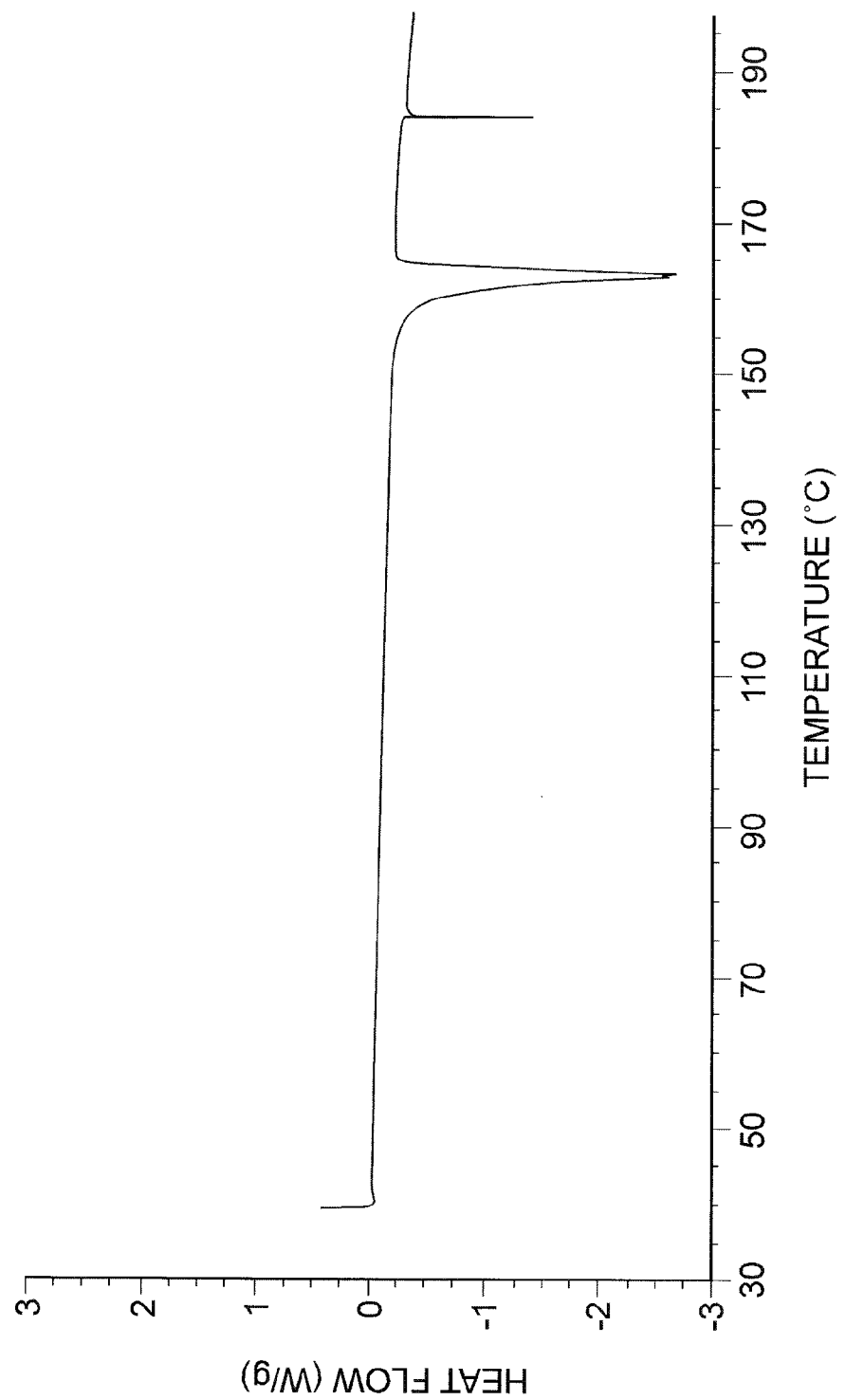
FIG. 7 is a DSC curve of crystalline bazedoxifene acetate Form D obtained in accordance with Example 36

2. The polymorph of claim 1, having a powder x-ray diffraction pattern with peaks located substantially in accordance with the pattern of FIG. 4.

3. The polymorph of claim 1 wherein said powder X-ray diffraction further comprises peaks at 2θ values of about 12.8, 13.4, 19.9, 23.3, or 34.6 degrees.

4. The polymorph of claim 1, wherein said powder X-ray diffraction further comprises peaks at 2θ values of about 9.9, 15.7, 17.1, or 20.5 degrees.

5. A process for preparing polymorph of claim 1, comprising:
   a) providing bazedoxifene free base in an alcohol solvent, an ether solvent, an ester solvent, a ketone solvent, a halogenated hydrocarbon solvent, a hydrocarbon solvent, a nitrile solvent, a dipolar aprotic solvent, water, or any mixtures thereof;
   b) adding a source of acetate ions; and
   c) maintaining the mixture of step b) for a time and under conditions suitable for formation of the crystalline of bazedoxifene acetate.

6. The process of claim 5 wherein the bazedoxifene free base used in step a) is crystalline bazedoxifene free base.

7. The process of claim 5 wherein the source of acetate ions used in step b) is acetic acid.

8. The process of claim 5, wherein the crystallization is initiated either by cooling or by addition of an anti-solvent or by both.

9. A process for preparing polymorph of claim 1, comprising:
   a) providing a mixture of bazedoxifene acetate in a suitable solvent;

b) adding seed crystals of crystalline bazedoxifene acetate and an anti-solvent; and c) isolating crystalline of bazedoxifene acetate.

10. The process of claim 9 wherein starting bazedoxifene acetate used in step a) is either in crystalline or in amorphous form.

11. The process of claim 9 wherein the solvent used in step a) is a ketone solvent, an ester solvent, a nitrile solvent, an alcohol solvent, or a mixture of any two or more thereof.

12. The process of claim 9 wherein the anti-solvent used in step b) is an aliphatic hydrocarbon solvent or an ether solvent.

13. A process of claim 12 wherein the anti-solvent is n-heptane.

14. Crystalline bazedoxifene free base.

15. The crystalline bazedoxifene free base of claim 14, wherein the bazedoxifene free base is an anhydrate.

16. The crystalline bazedoxifene free base of claim 14, having a powder X-ray diffraction pattern with peaks located substantially in accordance with the pattern of FIG. 1.

17. The polymorph (Form A) of crystalline bazedoxifene free base of claim 14 having powder X-ray diffraction peaks at 2θ values of about 11.3, 15.4, 15.8, 19.0, 19.3, 19.8, 22.3, or 22.7 degrees.

18. The polymorph of claim 17 having additional powder X-ray diffraction peaks at 2θ values of about 13.5, 14.1, 14.6, 16.5, 16.7, 17.5, 18.2, 23.4, or 23.7 degrees.

19. The polymorph of claim 15 having additional powder X-ray diffraction peaks at 2θ values of about 8.7, 9.5, 11.8, 12.8, 20.2, 21.3, 22.2, 24.7, 25.4, 26.5, 28.2, 29.3, or 33.7 degrees.

20. A process for the prepararation of crystalline bazedoxifene free base of claim 14 comprising:

a) either reacting an acid addition salt of bazedoxifene with a base to form bazedoxifene free base; or b) adjusting the pH of the aqueous phase of a mixture of an acid addition salt of bazedoxifene and a solvent comprising water to about 7-10 using a suitable base; and c) isolating the crystalline bazedoxifene free base.

21. The process of claim 20, wherein the pH of the aqueous phase is adjusted in step b) using an inorganic or organic base.

22. A solid pharmaceutical composition of bazedoxifene acetate comprising polymorph of claim 1 in association with one or more pharmaceutical acceptable carriers.

23. A process for the preparation of a pharmaceutically acceptable salt of bazedoxifene comprising:

a) providing a solution of crystalline bazedoxifene free base b) treating a mixture of step a) with a suitable acid.

24. A process according to claim 23, wherein the pharmaceutically acceptable salt is acetate.

* * * * *